US012170081B1

United States Patent
Ni et al.

(10) Patent No.: US 12,170,081 B1
(45) Date of Patent: Dec. 17, 2024

(54) SPEECH BRAIN-COMPUTER INTERFACE NEURAL DECODING SYSTEMS BASED ON CHINESE LANGUAGE AND IMPLEMENTATION METHODS THEREOF

(71) Applicant: TIANJIN UNIVERSITY, Tianjin (CN)

(72) Inventors: Guangjian Ni, Tianjin (CN); Ran Zhao, Tianjin (CN); Yanru Bai, Tianjin (CN); Hongxing Liu, Tianjin (CN); Mingkun Guo, Tianjin (CN); Qi Zheng, Tianjin (CN); Qi Tang, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 0 days.

(21) Appl. No.: 18/754,146

(22) Filed: Jun. 25, 2024

(30) Foreign Application Priority Data

Oct. 26, 2023 (CN) .......................... 202311395030.2

(51) Int. Cl.
*G10L 15/18* (2013.01)
*G10L 13/027* (2013.01)
(Continued)

(52) U.S. Cl.
CPC ........ *G10L 15/1815* (2013.01); *G10L 13/027* (2013.01); *G10L 13/047* (2013.01);
(Continued)

(58) Field of Classification Search
CPC . G10L 15/1815; G10L 13/027; G10L 13/047; G10L 15/063; G10L 15/16; G10L 15/24; G10L 25/18
See application file for complete search history.

(56) References Cited

U.S. PATENT DOCUMENTS

| 11,640,204 B2* | 5/2023 | Shenoy | .................... G06F 18/41 |
| | | | 345/156 |
| 2013/0184558 A1* | 7/2013 | Gallant | ................ A61B 5/0042 |
| | | | 600/409 |

(Continued)

FOREIGN PATENT DOCUMENTS

| CN | 106726030 A | 5/2017 |
| CN | 111310783 A | 6/2020 |

(Continued)

OTHER PUBLICATIONS

Kingma, et al., "Generative flow with invertible 1x1 convolutions." Advances in Neural Information Processing Systems, pp. 10215-10224, 2018. (Year: 2018).*

(Continued)

*Primary Examiner* — Fariba Sirjani
(74) *Attorney, Agent, or Firm* — METIS IP LLC

(57) ABSTRACT

A speech brain-computer interface neural decoding system based on Chinese language, a method for controlling the speech brain-computer interface neural decoding system, and a method for implementing the speech brain-computer interface neural decoding system are disclosed. The speech brain-computer interface neural decoding system includes an electroencephalography (EEG) data acquisition module, a significance feature screening and verification module, a speech imagery EEG data decoding module, and an understandable speech synthesis module. The speech brain-computer interface neural decoding system integrates EEG data collection, EEG feature extraction, EEG feature screening, EEG signal decoding for reconstructing speech spectrum information and understandable speech synthesis. After obtaining reconstructed spectrogram features, a Pearson correlation analysis may be performed with original spectrogram features, with a correlation generally being ≥80%. The decoding performance of the speech brain-computer (Continued)

interface neural decoding system is superior to traditional decoding models, effectively improving communication between patients with speech disorders and the outside world.

9 Claims, 8 Drawing Sheets

(51) Int. Cl.
  *G10L 13/047* (2013.01)
  *G10L 15/06* (2013.01)
  *G10L 15/16* (2006.01)
  *G10L 15/24* (2013.01)
  *G10L 25/18* (2013.01)

(52) U.S. Cl.
  CPC ............ *G10L 15/063* (2013.01); *G10L 15/16* (2013.01); *G10L 15/24* (2013.01); *G10L 25/18* (2013.01)

(56) References Cited

U.S. PATENT DOCUMENTS

| | | | |
|---|---|---|---|
| 2019/0107888 A1* | 4/2019 | Sereshkeh | A61B 5/374 |
| 2019/0295566 A1* | 9/2019 | Moghadamfalahi | A61B 5/318 |
| 2020/0142481 A1 | 5/2020 | Lee et al. | |
| 2021/0064135 A1* | 3/2021 | Shenoy | G06N 3/044 |
| 2021/0365726 A1* | 11/2021 | Jie | G06F 18/211 |
| 2023/0067026 A1* | 3/2023 | Huts | G06V 20/00 |
| 2023/0096021 A1* | 3/2023 | Trockman | G06N 3/084 |
| | | | 382/156 |
| 2024/0194198 A1* | 6/2024 | Lee | A61B 5/372 |

FOREIGN PATENT DOCUMENTS

| | | |
|---|---|---|
| CN | 112001306 A | 11/2020 |
| CN | 113031766 A | 6/2021 |
| CN | 113625870 A | 11/2021 |
| CN | 115153563 A | 10/2022 |
| CN | 115517687 A | 12/2022 |
| CN | 116312531 A | 6/2023 |
| CN | 116364096 A | 6/2023 |
| WO | 2022251472 A1 | 12/2022 |
| WO | 2023040588 A1 | 3/2023 |

OTHER PUBLICATIONS

First Office Action in Chinese Application No. 202311395030.2 mailed on Dec. 1, 2023, 20 pages.

Decision to Grant a Patent in Chinese Application No. 202311395030.2 mailed on Jan. 4, 2024, 4 pages.

* cited by examiner

SPEECH BRAIN-COMPUTER INTERFACE NEURAL DECODING SYSTEMS BASED ON CHINESE LANGUAGE AND IMPLEMENTATION METHODS THEREOF

CROSS-REFERENCE TO RELATED APPLICATIONS

This application claims priority to Chinese Patent Application No. 202311395030.2, filed on Oct. 26, 2023, the entire contents of which are incorporated herein by reference.

TECHNICAL FIELD

The present disclosure relates to the field of brain-computer interface (BCI) technology, and in particular, to speech brain-computer interface neural decoding systems based on Chinese language and implementation methods thereof.

BACKGROUND

Communication is a vital part of daily life. However, for a patient with a speech disorder and others who cannot produce normal vocal sounds, communicating with the outside world is challenging, and in severe cases, they may entirely lose the ability to speak. With the advancement of electroencephalography (EEG) technology and the emergence of BCI technology, such as a P300 speller, a steady-state visual evoked potential (SSVEP) speller, motor imagery (MI), or the like, a specific neural activity may be converted into a computer instruction to aid communication.

A currently emerging BCI paradigm is speech imagery, which is also referred to as covert speech, inner speech, or verbal thinking. The speech imagery involves internal speech activity without an explicit movement of any articulatory organs and is related to the brain's neural mechanisms for cognition, memory, learning, thinking, or the like. Research on neural decoding of speech imagery has made some progress. Subject groups studied include normal individuals, speech disorder patients (e.g., patients with aphasia and dysarthria), and individuals unable to produce normal vocal sounds due to brain injuries or motor neuron diseases. Most of research materials for speech imagery neural decoding are in non-tonal languages like English and Spanish, and there are few reports on neural decoding of speech imagery in tonal languages like Chinese. Chinese, being a unique tonal language and the most widely spoken language in the world, offers broad research prospects and diversity. Existing studies mainly focus on extraction of EEG features for classification and design of classifiers, aiming only at classification of speech imagery EEG data without further research on semantic decoding of speech imagery.

A strategy of speech imagery is similar to the use of MI in helping paralyzed patients control external devices. However, for individuals with congenital or long-term motor impairments, motor imagery may be difficult or impossible.

Considering that speech is a fundamental and natural form of human communication, subjects generally does not require training during speech imagery. Additionally, with reduced external stimuli, subjects may spontaneously engage in speech imagery, which is more conducive to assisting patients with speech disorders in communicating with the outside world. Conducting research on the neural decoding of speech imagery is expected to significantly improve the quality of life for patients with speech disorders in the near future.

SUMMARY

A purpose of the present disclosure is to address the deficiency in research on Chinese language speech imagery neural decoding in the prior art by providing a speech brain-computer interface neural decoding system based on Chinese language.

One or more embodiments of the present disclosure provide a speech brain-computer interface neural decoding system based on Chinese language. The system may include an electroencephalography (EEG) data acquisition module, a significance feature screening and verification module, a speech imagery EEG data decoding module, and an understandable speech synthesis module.

The electroencephalography (EEG) data acquisition module may be configured to collect EEG data during speech imagery.

The significance feature screening and verification module may be configured to perform feature extraction on features from the EEG data, verify the separability of the features, and screen the features to obtain EEG data with a specific frequency band or EEG data within a brain region The speech imagery EEG data decoding module may be configured to obtain, by inputting the EEG data with the specific frequency band or the EEG data within the brain region into a speech imagery semantic decoder for decoding and reconstructing, speech spectrum information, wherein the speech imagery semantic decoder includes a spatial attention layer, a convolutional layer, a subject layer, a convolutional block, a Batch Norm layer, a GELU activation layer, and two 1×1 convolutional layers.

The understandable speech synthesis module may be configured to synthesize the speech spectrum information into real speech using a speech synthesis technology.

A decoding process of the speech imagery semantic decoder may include:
  S1: remapping the EEG data with the specific frequency band or the EEG data within the brain region onto the spatial attention layer;
  S2: outputting the EEG data with the specific frequency band or the EEG data within the brain region to the convolutional layer for convolution via Fourier spatial parameterization of each output channel of the spatial attention layer, respectively, and reducing dimensionality of the EEG data at the same time;
  S3: aligning EEG signals in a common space by training using the subject layer;
  S4: performing convolution by using the convolutional block;
  S5: halving a count of channels using the BatchNorm layer and the GELU activation layer; and
  S6: utilizing an inter-object variability by applying the two 1×1 convolutional layers, outputting a matching speech representation, and utilizing a wav2vec 2.0 speech algorithm for automatic learning to obtain the speech spectrum information.

In some embodiments, the feature extraction may include frequency domain feature extraction and spatial feature extraction. The frequency domain feature extraction may be performed to obtain a signal spectrum with the specific frequency band by performing power spectrum analysis on the EEG data using an autoregressive model. The spatial feature extraction may be performed to identify a connectivity index closely related to the speech imagery by adopting brain network connectivity analysis and selecting a Granger causality-based index to measure a causal relationship or an information flow direction between different neural oscillatory activities.

In some embodiments, a count of channels of the spatial attention layer may be the same as a count of sensor channels for original collection of the EEG data, and the convolutional block may include three convolutional layers.

In some embodiments, the EEG data acquisition module, the EEG data acquisition module, the significance feature screening and verification module, the speech imagery EEG data decoding module, and the understandable speech synthesis module may be integrated in a visualization program to obtain the speech brain-computer interface neural decoding system.

One or more embodiments of the present disclosure provide a method for controlling the speech brain-computer interface neural decoding system. The method may include:
  collecting EEG data during speech imagery from a specific population;
  performing feature extraction on features from the EEG data, and screening the features to obtain EEG data with a specific frequency band or EEG data within a brain region;
  obtaining, by inputting the EEG data with the specific frequency band or the EEG data within the brain region into a speech imagery semantic decoder for decoding and reconstructing, speech spectrum information; and
  synthesizing the speech spectrum information into real speech using a speech synthesis technology, and completing an end-to-end output of the EEG data to the real speech.

One or more embodiments of the present disclosure provide a method for implementing the speech brain-computer interface neural decoding system. The method may include:
  according to an experimental paradigm design, collecting EEG data of a subject during speech imagery and normal vocalization and speech data of the subject during normal vocalization, and constructing a speech imagery EEG database;
  performing pre-processing and feature extraction on features from the EEG data in the speech imagery EEG database, verifying separability of the features, screening the features to obtain EEG data with a specific frequency band or EEG data within a brain region, and extracting an acoustic feature of speech data corresponding to the EEG data with the specific frequency band or the EEG data within the brain region using a long and short-term memory (LSTM) network at the same time;
  designing a single end-to-end architecture using a deep learning algorithm, determining a generic task of neural decoding, and initially constructing a speech imagery semantic decoder;
  training the constructed speech imagery semantic decoder using the EEG data with the specific frequency band or the EEG data within the brain region and the acoustic feature of the speech data corresponding to the EEG data with the specific frequency band or the EEG data within the brain region; and
  integrating the EEG data acquisition, the EEG feature extraction, the EEG feature screening, and the speech imagery semantic decoder in the above operations to obtain the brain-computer interface control system.

In some embodiments, an inclusion criterion for the subject is an absence of any history of hearing or visual impairment, neurological disorders, or other speech disorders; and in the course of an experiment, an auditory cueing vocalization material and a visual cueing material may be selected according to corpus screening guidelines.

In some embodiments, a training process of the speech imagery semantic decoder may include:
  calibrating and aligning the EEG data with the specific frequency band or the EEG data within the brain region with the acoustic feature of the speech data corresponding to the EEG data with the specific frequency band or the EEG data within the brain region, and establishing a mapping relationship;
  dividing the aligned data into a training set, a validation set, and a test set, inputting data in the training set into the speech imagery semantic decoder, reconstructing and obtaining speech spectrum information corresponding to the EEG data with the specific frequency band or the EEG data within the brain region, and performing comparative learning training on the speech imagery semantic decoder; and
  performing validation and testing using the validation set and the test set.

In some embodiments, a model parameter corresponding to an optimal decoding performance may be used as initialization during the training process by sharing acoustic features among subjects, then fine-tuning may be performed when training EEG data of other subjects, and transfer learning may be used to accelerate model convergence and improve a generalization ability of the speech imagery semantic decoder.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
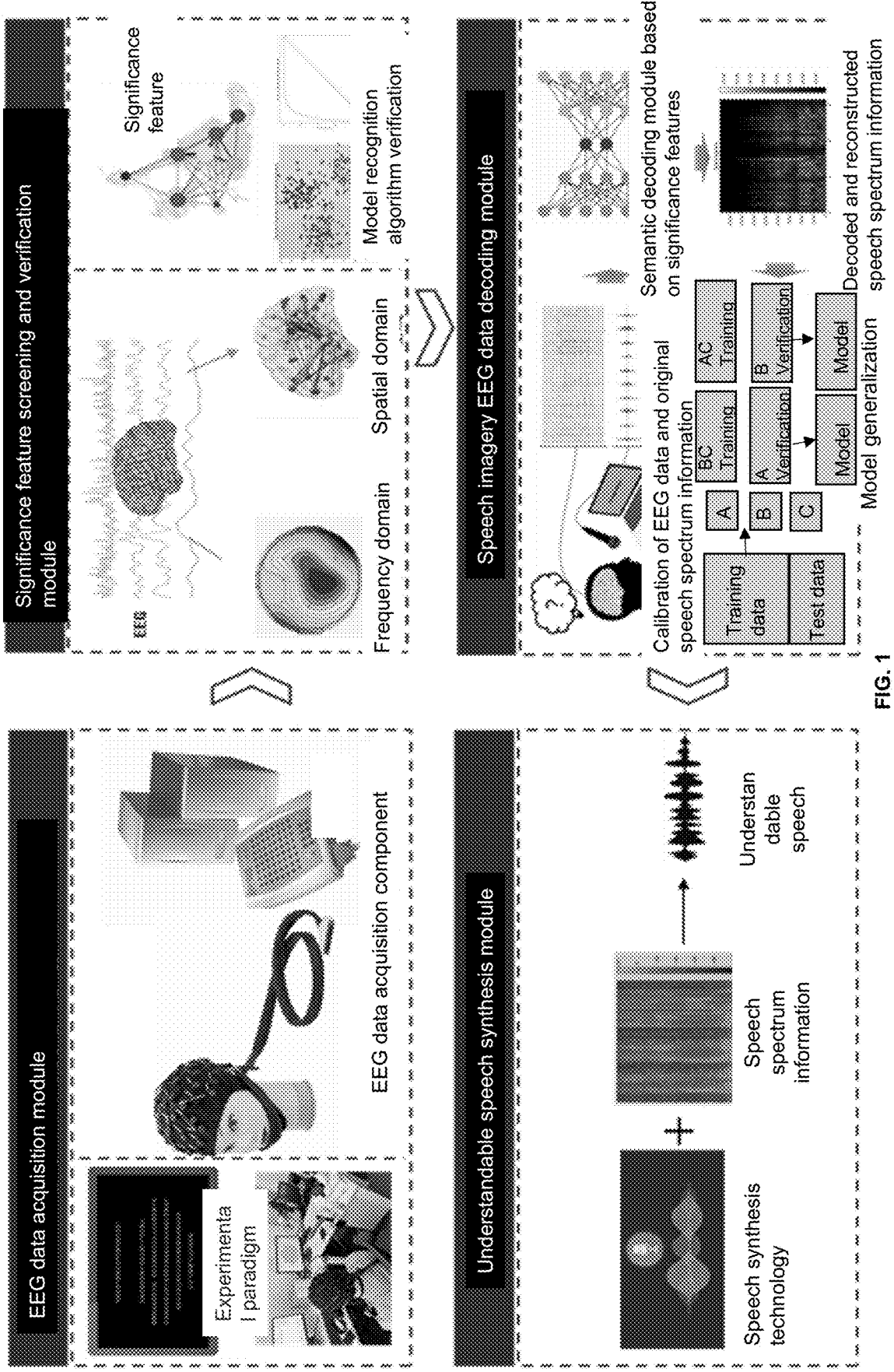
FIG. 1 is a schematic diagram illustrating an overall architecture of a speech brain-computer interface neural decoding system based on Chinese language according to some embodiments of the present disclosure.

In order to more clearly illustrate the technical solutions of the embodiments of the present disclosure, the accompanying drawings to be used in the description of the embodiments will be briefly described below. Obviously, the accompanying drawings in the following description are only some examples or embodiments of the present disclosure, and that the present disclosure may be applied to other similar scenarios in accordance with these drawings without creative labor for those of ordinary skill in the art. Unless obviously acquired from the context or the context illustrates otherwise, the same numeral in the drawings refers to the same structure or operation.

It should be understood that "system," "device," "unit," and/or "module" as used herein is a way to distinguish between different components, elements, parts, sections, or assemblies at different levels. However, these words may be replaced by other expressions if they accomplish the same purpose.

As indicated in the present disclosure and in the claims, the singular forms "a," "an," and "the" may be intended to include the plural forms as well, unless the context clearly indicates otherwise. In general, the terms "comprise," "comprises," and/or "comprising," "include," "includes," and/or "including," when used in this disclosure, specify the presence of stated features, integers, steps, operations, elements, and/or components, but do not preclude the presence or addition of one or more other features, integers, steps, operations, elements, components, and/or groups thereof.

Flowcharts are used in the present disclosure to illustrate the operations performed by the system according to some embodiments of the present disclosure. It should be understood that the operations described herein are not necessarily executed in a specific order. Instead, the operations may be executed in reverse order or simultaneously. Additionally, one or more other operations may be added to these processes, or one or more operations may be removed from these processes.

Figure 2:
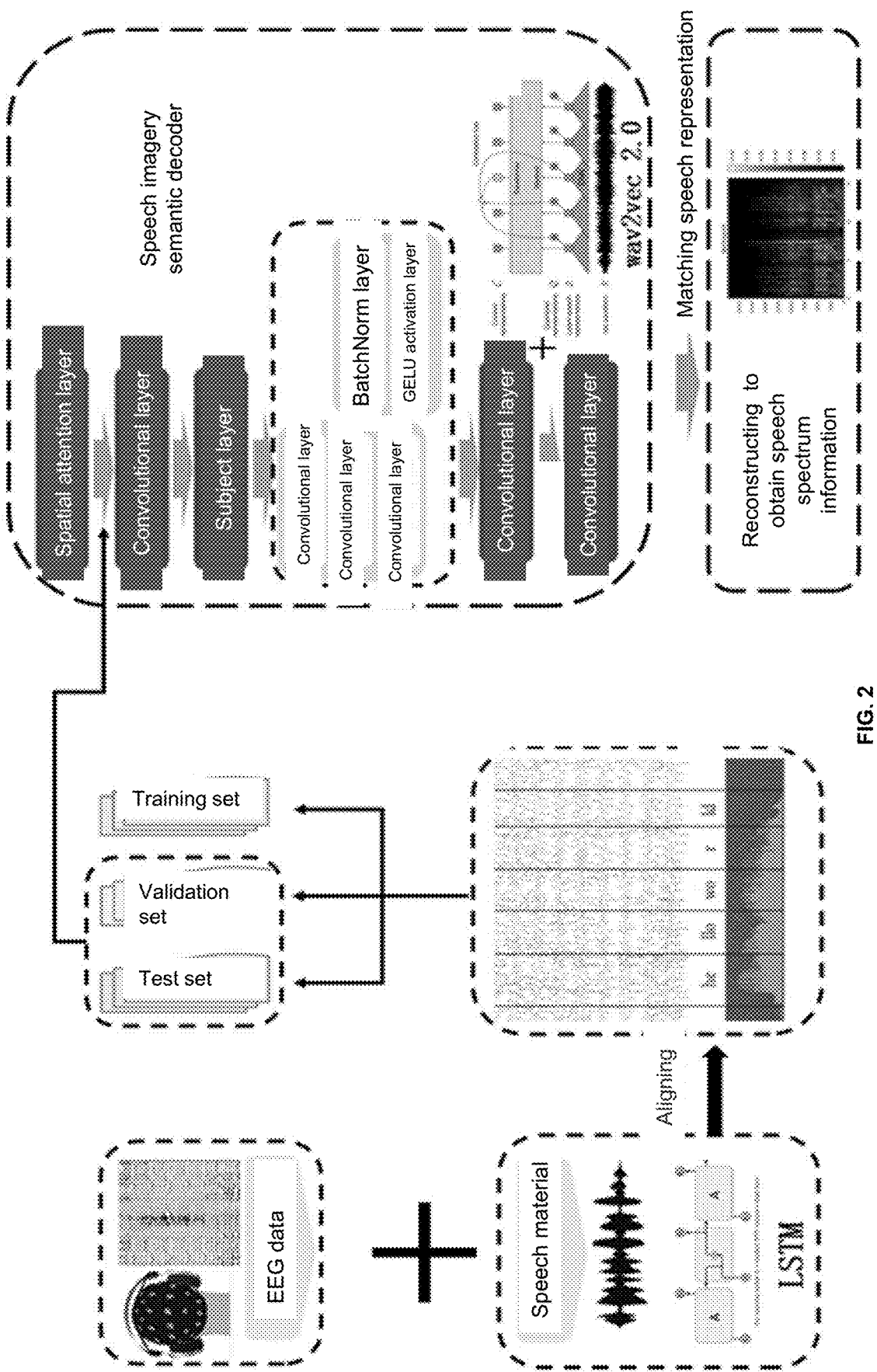
FIG. 2 is a schematic diagram illustrating a structure and a training process of a speech imagery semantic decoder according to some embodiments of the present disclosure.
Figure 3:
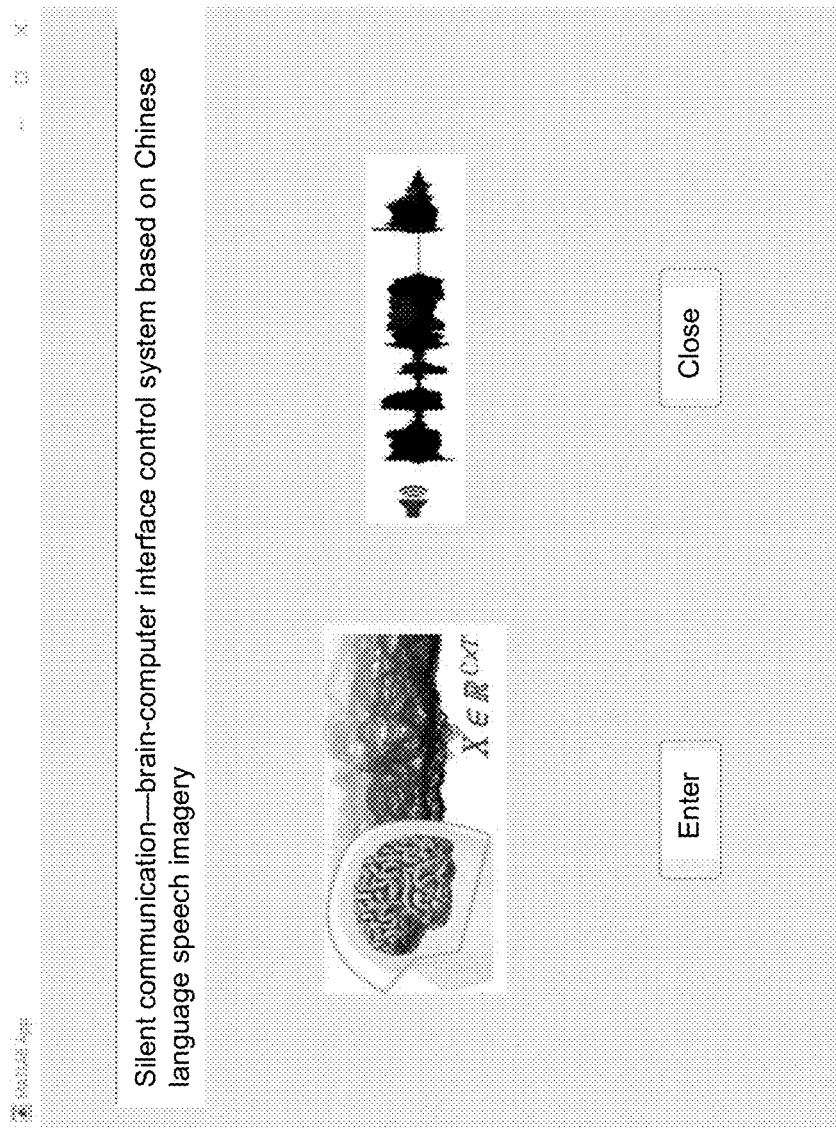
FIG. 3 is a schematic diagram illustrating a first page of an interface of an integrated visualization system according to some embodiments of the present disclosure.
Figure 4:
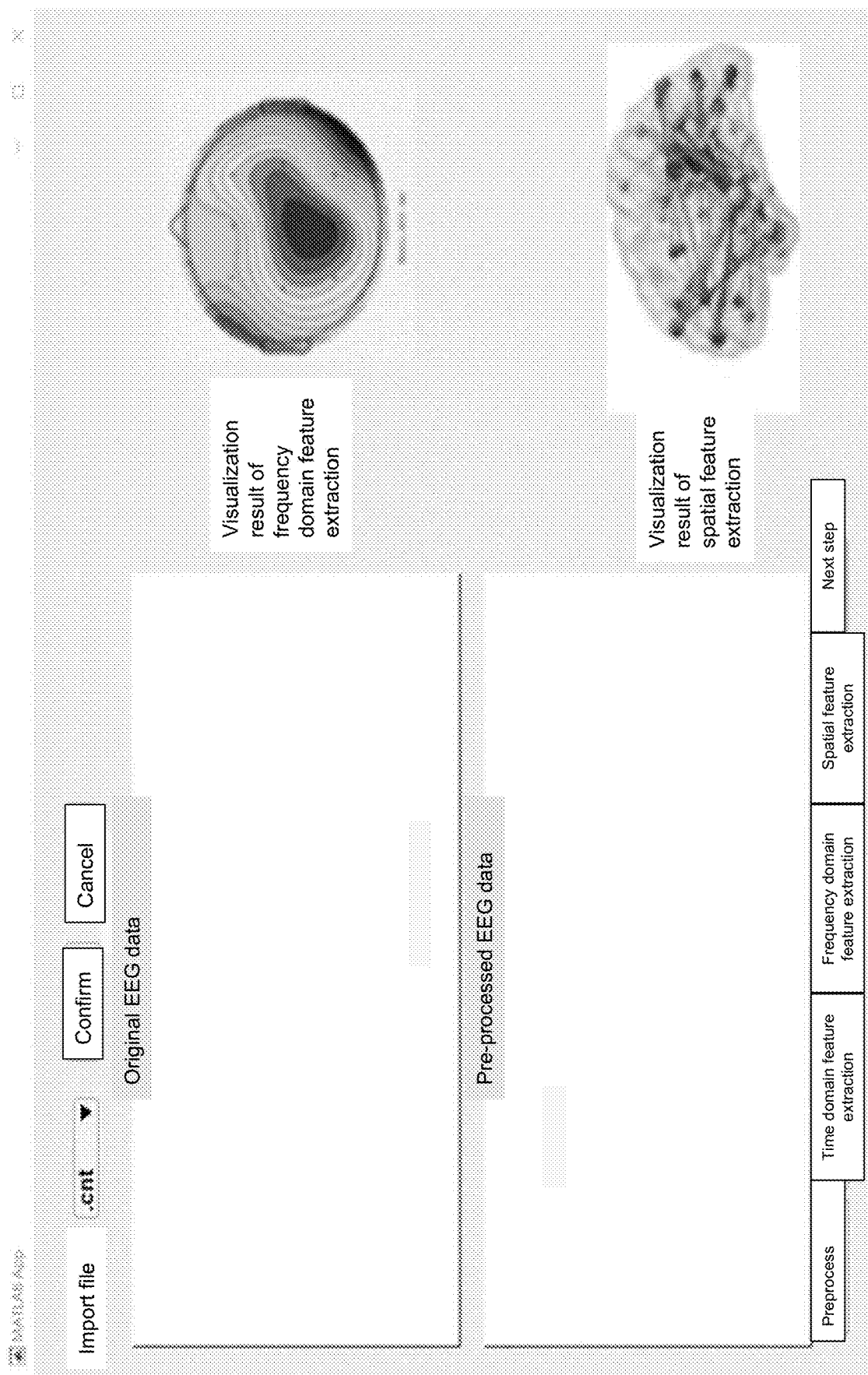
FIG. 4 is a schematic diagram illustrating an EEG data processing interface of an integrated visualization system according to some embodiments of the present disclosure.
Figure 5:
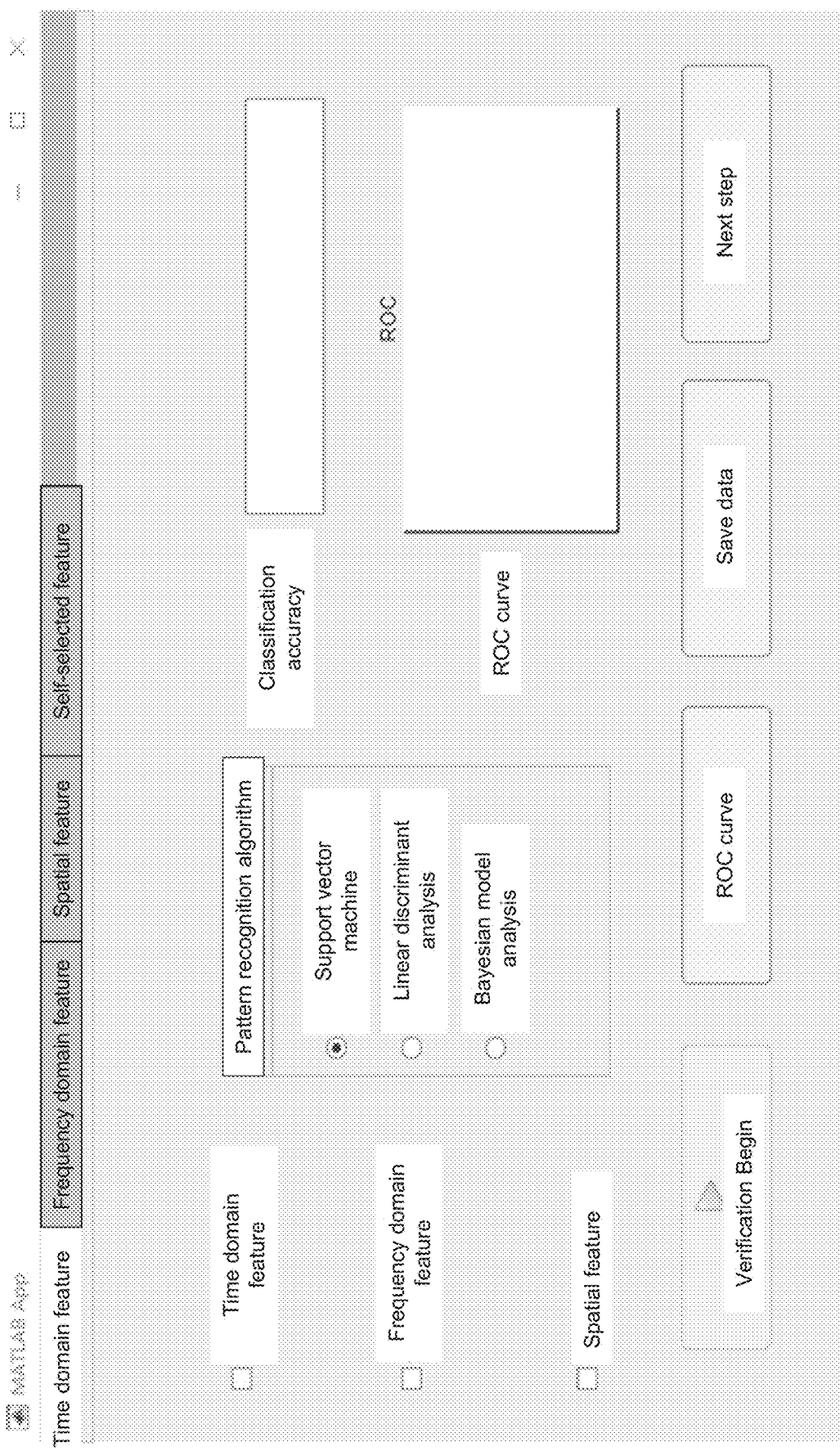
FIG. 5 is a schematic diagram illustrating a specificity EEG feature separability verification interface of an integrated visualization system according to some embodiments of the present disclosure.
Figure 6:
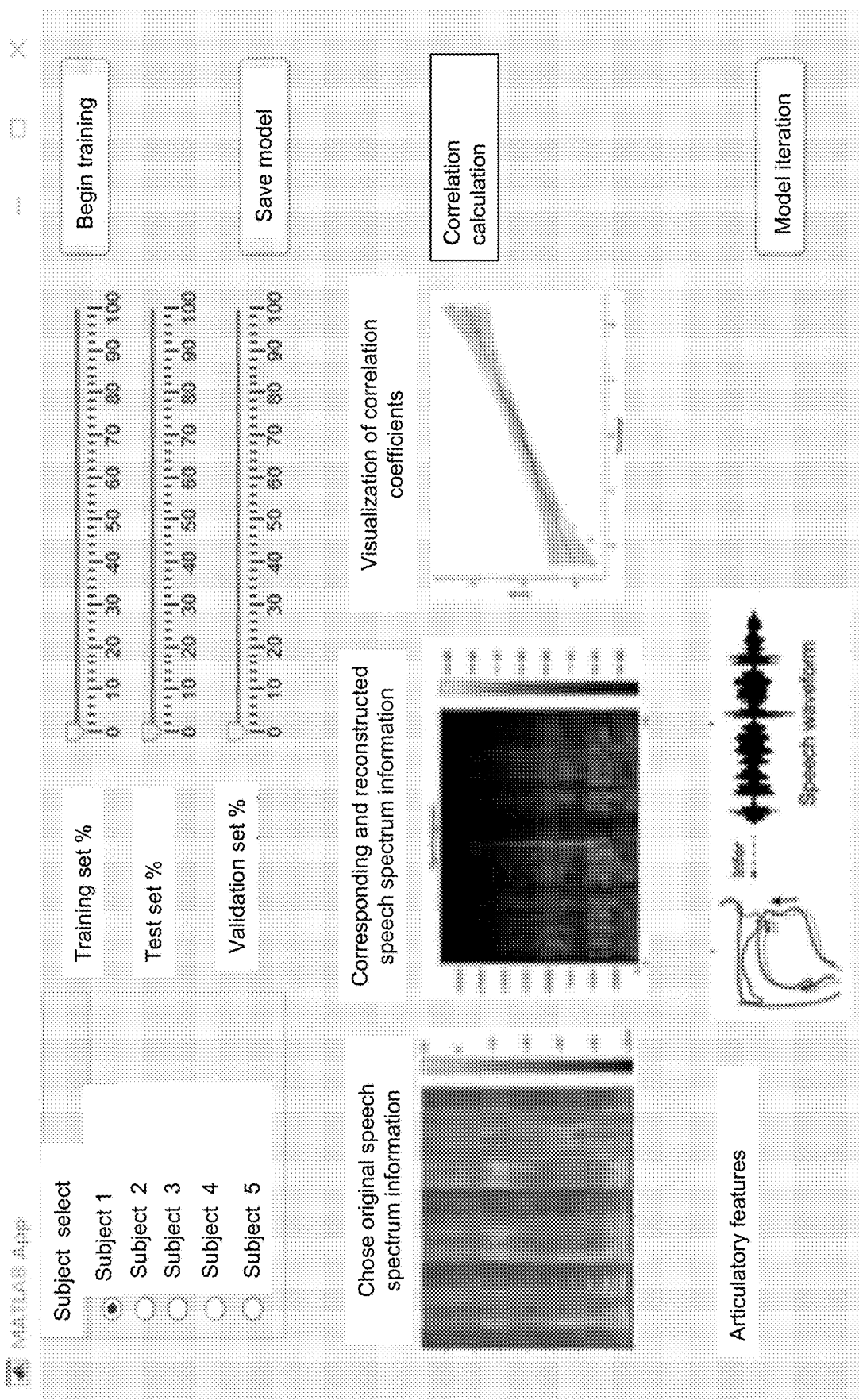
FIG. 6 is a schematic diagram illustrating a decoding model training interface of an integrated visualization system according to some embodiments of the present disclosure.
Figure 7:
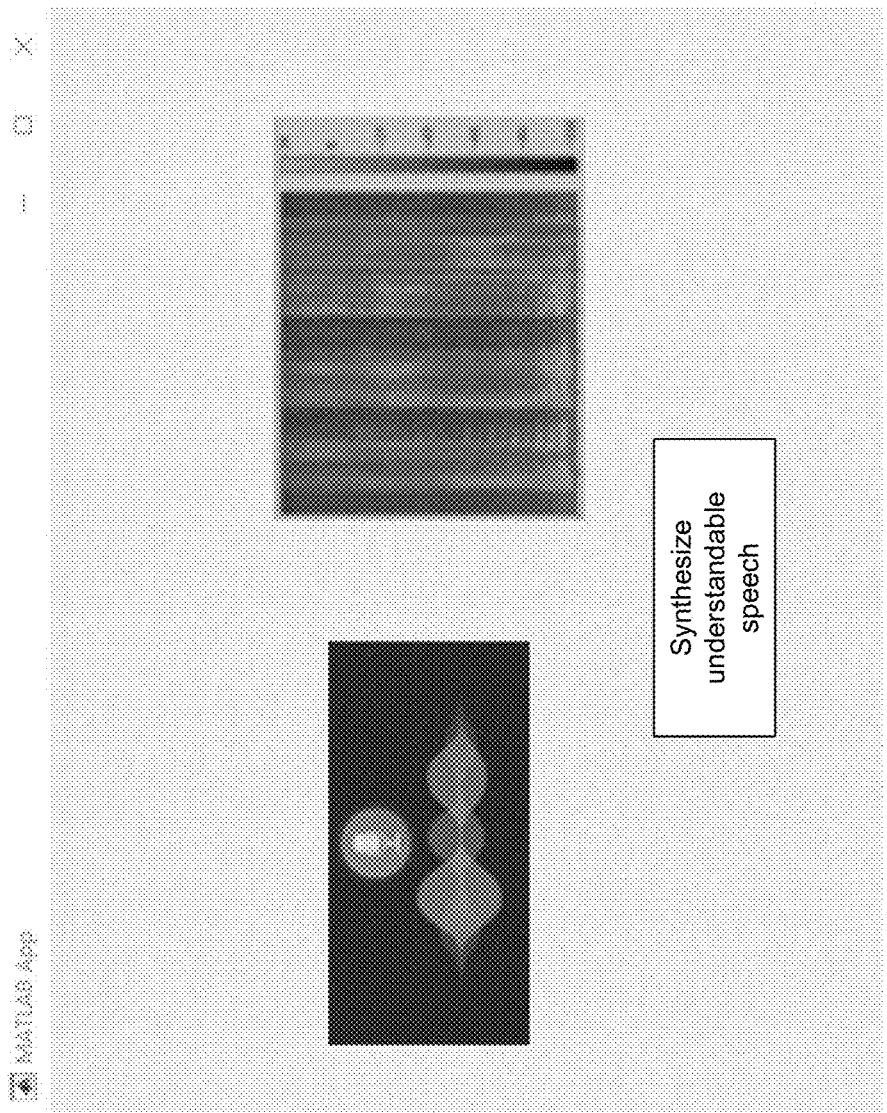
FIG. 7 is a schematic diagram illustrating an understandable speech synthesis interface of an integrated visualization system according to some embodiments of the present disclosure.

FIG. 1 is a schematic diagram illustrating an overall architecture of a speech brain-computer interface neural decoding system based on Chinese language according to some embodiments of the present disclosure. FIG. 2 is a schematic diagram illustrating a structure and a training process of a speech imagery semantic decoder according to some embodiments of the present disclosure. FIG. 3 is a schematic diagram illustrating a first page of an interface of an integrated visualization system according to some embodiments of the present disclosure. FIG. 4 is a schematic diagram illustrating an EEG data processing interface of an integrated visualization system according to some embodiments of the present disclosure. FIG. 5 is a schematic diagram illustrating a specificity EEG feature separability verification interface of an integrated visualization system according to some embodiments of the present disclosure. FIG. 6 is a schematic diagram illustrating a decoding model training interface of an integrated visualization system according to some embodiments of the present disclosure. FIG. 7 is a schematic diagram illustrating an understandable speech synthesis interface of an integrated visualization system according to some embodiments of the present disclosure.

Some embodiments of the present disclosure provide a speech brain-computer interface neural decoding system based on Chinese language as shown in FIG. 1, which includes an electroencephalogram (EEG) data acquisition module, a significance feature screening and verification module, a speech imagery EEG data decoding module, and an understandable speech synthesis module.

The EEG data acquisition module may be configured to collect EEG data during speech imagery.

The EEG data may reflect information about brain activity of a subject. For example, the EEG data may include frequencies and intensities of EEG activity in different regions of the scalp.

In some embodiments, the EEG data acquisition module may include a signal acquisition component described later (e.g., a sensor for original collection of the EEG data or a 64-channel Neuroscan EEG acquisition device as described below), and by wearing the signal acquisition component on the head of the subject, a plurality of disc electrodes are adhered to the subject's scalp to form a conduction channel, so that electrical signals of neurons in the subject's brain during speech imagery, i.e., the EEG data during speech imagery, may be obtained. The subject refers a subject from whom the EEG data is being collected.

The significance feature screening and verification module may be configured to perform preprocessing and feature extraction on features form the EEG data, verify separability of the features, and screen the features to obtain EEG data with a specific frequency band or EEG data within a brain region.

The specific frequency band refers to the EEG frequency band closely related to speech imagery. In some embodiments, EEG frequency bands are mainly divided into the $\delta$ (0.5 Hz~4 Hz) band, $\theta$ (4 Hz~8 Hz) band, $\alpha$ (8 Hz~12 Hz) band, $\beta$ (12 Hz~30 Hz) band, and $\gamma$ (>30 Hz) band. In some embodiments, the significance feature screening and verification module may determine the band power of the aforementioned frequency bands based on EEG data during speech imagery through processes such as Fourier transform, and/or obtain the band energy of the aforementioned frequency bands by integrating the EEG data. Then, based on the band power and band energy of the aforementioned frequency bands, statistical analysis may be performed to determine a frequency band with a significant difference as the specific frequency band.

In some embodiments, the specific frequency band may include the $\delta$ (0.5 Hz~4 Hz) band, $\alpha$ (8 Hz~12 Hz) band, and $\beta$ (12 Hz~30 Hz) band.

The preprocessing includes electrodes location, culling extraneous electrodes, filtering, downsampling, segmenting, baseline correcting, interpolating bad leads, culling bad segments, conducting independent component analysis, culling artifacts, re-referencing, or the like.

The feature extraction may include frequency domain feature extraction and spatial feature extraction. The frequency domain feature extraction may be performed to obtain a signal spectrum with the specific frequency band by performing power spectrum analysis on the EEG data using an autoregressive model. The spatial feature extraction may be performed to identify a connectivity index closely related to the speech imagery by adopting brain network connectivity analysis and selecting a Granger causality-based index to measure a causal relationship or an information flow direction between different neural oscillatory activities.

The separability of the features refers to a degree of distinction or separability between different feature categories obtained after preprocessing and feature extraction of the EEG data. More descriptions of determining the separability may be found in the subsequent related descriptions.

The speech imagery EEG data decoding module may be configured to obtain speech spectrum information by inputting the EEG data with the specific frequency band or EEG data within the brain region into a speech imagery semantic decoder for decoding and reconstructing.

The speech imagery semantic decoder may be used to translate a subject's brain activity during speech imagery into a continuous stream of text or audio.

The speech spectrum information refers to the spectrum information of speech. Exemplary speech spectrum information may include a tone of voice, a distribution of energy in the voice, or the like. More descriptions of obtaining the speech spectrum information using the speech imagery semantic decoder may be found in FIG. 2 and the relevant descriptions thereof.

The understandable speech synthesis module may be configured to synthesize the speech spectrum information into real speech using a speech synthesis technology.

The above modules may be integrated in a visualization program, resulting in a communication-assistive brain-computer interface system that conforms to a natural vocalization manner with a high communication rate. Visualization interfaces of the system are shown in FIG. 3 to FIG. 7. Intelligible real speech can be outputted by simply collecting the EEG data of the subject's speech imagery, which truly enables intuitive, high communication rate communication between speech-impaired patients and the outside world, thereby assisting speech-impaired patients in communicating with the outside world.

In some embodiments, the speech imagery semantic decoder may include a spatial attention layer, a convolutional layer, a subject layer, a convolutional block, a BatchNorm layer, a GELU activation layer, and two 1×1 convolutional layers, as shown in FIG. 2. A count of channels of the spatial attention layer may be the same as a count of sensor channels for original collection of the EEG data, and the convolutional block may include three convolutional layers. For ease of differentiation, the convolutional layer between the spatial attention layer and the subject layer is subsequently referred to as the first convolutional layer, and the three convolutional layers included in the convolutional block are referred to as the second convolutional layer.

In some embodiments, a decoding process of the speech imagery semantic decoder may include:

S1: the EEG data with the specific frequency band or the EEG data within the brain region may be remapped by the speech imagery semantic decoder onto the spatial attention layer whose count of channels is the same as the count of sensor channels for original collection of the EEG data;

S2: each output channel of the spatial attention layer may output the EEG data with the specific frequency band or the EEG data within the brain region to the convolutional layer for convolution via Fourier spatial parameterization, respectively, and dimensionality of the EEG data may be reduced at the same time;

Each output channel of the spatial attention layer may output the EEG data with the specific frequency band or the EEG data within the brain region through Fourier spatial parameterization respectively, thereby obtaining parameterized EEG data.

In some embodiments, an input of the spatial attention layer may include the EEG data with the specific frequency band or the EEG data within the brain region, and an output of the spatial attention layer may include the parameterized EEG data. In some embodiments, an input of the convolutional layer may include the parameterized EEG data, and an output of the convolutional layer may include convolved EEG data.

S3: EEG signals may be aligned in a common space by training using the subject layer (i.e., a convolutional layer without an activation function);

An input of the subject layer may include the convolved EEG data, and an output of the subject layer may include the EEG signals.

In some embodiments, the subject layer may be trained based on a large number of labeled training samples. The training samples for the subject layer include EEG data after sample convolution, and the labels include actual EEG signals corresponding to the training samples.

In some embodiments, the training samples may be determined based on historical data, and the labels may be determined through manual annotation or other techniques. In some embodiments, a training process of the subject layer may include:

inputting the training samples into an initial subject layer, constructing a loss function based on an output of the initial subject layer and the labels, and iteratively updating parameters of the initial subject layer based on the loss function. The training ends when a preset condition is met, and the trained subject layer is obtained. The preset condition may include, but is not limited to, the loss function converging, the training cycle reaching a threshold, etc.

S4: convolution may be performed by using the convolutional block, wherein the first two second convolutional layers use residual skip connections and increase dilation, and the last second convolutional layer decreases dimensionality.

Reducing dimensionality refers to reducing the dimensions of the EEG signals processed by the first two second convolutional layers. For example, reducing the dimensions of the EEG signals from three dimensions to two dimensions.

In some embodiments, an input of the convolutional block may include the EEG signals, and an output of the convolutional block may include EEG signals after multiple convolutions.

S5: a count of channels may be halved using the BatchNorm layer and the GELU activation layer;

The count of channels described above may be understood as the count of channels of the EEG signals after multiple convolutions performed by the convolution block.

In some embodiments, the BatchNorm layer and the GELU activation layer may halve that count of channels in various ways. Exemplary halving manners may include, but are not limited to, downsampling, grouped convolution, or the like. In some embodiments, the BatchNorm layer and the GELU activation layer may be structured as a single layer, whose input may include the EEG signals after multiple convolutions, and whose output may include the EEG signals after the count of channels is halved.

S6: The decoder may utilize an inter-object variability by applying the two 1×1 convolutional layers, output a matching speech representation, and then utilize a wav2vec 2.0 speech algorithm for extensive training to automatically learn to obtain the speech spectrum information.

In some embodiments, the two 1×1 convolutional layers may be structured as a single layer, whose input may include the EEG signals after the count of channels has been halved, and whose output may include a matched speech representation. The matched speech representation refers to audio information that corresponds to the EEG data with the specific frequency band or the EEG data within the brain region.

It should be noted that in addition to the wav2vec 2.0 speech algorithm, speech algorithms such as HuBERT may also be used.

In some embodiments, the EEG data acquisition module may include a signal acquisition component (e.g., a 64-channel Neuroscan EEG acquisition device as described later) and an EEG amplifier.

The signal acquisition component refers to a device or apparatus used to acquire the EEG data during speech imagery of a subject. For example, the signal acquisition component may be a 64-channel Neuroscan EEG acquisition device (with a sampling rate of 1 KHz and electrodes covering the entire head of the subject) as described later, wherein the signal acquisition component includes a plurality of disk electrodes. More descriptions of the signal acquisition component may be found in FIG. 8 and the related descriptions thereof.

The EEG amplifier refers to a device that is used to amplify the EEG data collected by the signal acquisition component. In some embodiments, the EEG amplifier may include a plurality of interfaces, each of which may be coupled to one of the plurality of disk electrodes of the signal acquisition component to amplify the EEG data collected by the signal acquisition component, thereby enhancing detection sensitivity and accuracy of the signal for subsequent analysis.

In some embodiments, the speech brain-computer interface neural decoding system may further include a control module, which may be implemented by a processor, and the control module may be connected with the EEG data acquisition module and the significance feature screening and verification module through a communication connection.

In some embodiments, the control module may be configured to: obtain, from the significance feature screening and verification module, classification accuracies of a plurality of dimensions obtained in the course of verifying the separability of the features, each of the plurality of dimensions corresponding to a combination of a feature extraction type and a pattern recognition algorithm; determine an average accuracy based on the classification accuracies of the plurality of dimensions; generate a multiplicity adjustment instruction and/or a sampling rate adjustment instruction in response to determining that the average accuracy is lower than a first threshold; and send the multiplicity adjustment instruction and/or the sampling rate adjustment instruction to the EEG amplifier and/or the signal acquisition component, respectively.

The amplification rate adjustment instruction may be used to adjust a signal amplification rate of the EEG amplifier to a target amplification rate; and the sampling rate adjustment instruction may be used to adjust a sampling rate of the signal acquisition component to a target sampling rate.

The processor may process data and/or information obtained from other devices or system components. The processor may execute program instructions based on the obtained data, information, and/or processing results to perform one or more of the functions described in the present disclosure. In some embodiments, the processor may include one or more sub-processing devices (e.g., one or more single-core processing devices or one or more multi-core multi-core processing devices). Merely by way of example, the processor may include a central processing unit (CPU), a controller, a microprocessor, or any combination thereof. In some embodiments, the processor may be integrated within the control module.

The communication connection refers to a way for facilitating information and/or data transfer interactions between devices. In some embodiments, the communication connection may include a wired connection (e.g., fiber optic, etc.) and a wireless connection (e.g., Bluetooth, WIFI, etc.).

The feature extraction type refers to a type of extraction manner used to characterize the EEG data collected by the signal acquisition component. In some embodiments, the feature extraction type may be the frequency domain feature extraction or the spatial feature extraction. In some embodiments, the feature extraction type may be a combination of the frequency domain feature extraction and the spatial feature extraction. More descriptions of the frequency domain feature extraction and the spatial feature extraction may be found in the relevant descriptions above.

The pattern recognition algorithm refers to a way for recognizing relevant patterns from a large amount of observed data, discriminating similarities, and making decisions. Exemplary pattern recognition algorithms may include support vector machine (SVM), linear discriminant analysis (LDA), Bayesian model analysis, or the like.

In some embodiments, each of the plurality of dimensions corresponding to a combination of a feature extraction type and a pattern recognition algorithm may include a combination of the frequency domain feature extraction and the support vector machine, a combination of the frequency domain feature extraction and the linear discriminant analysis (LDA), a combination of the frequency domain feature extraction and the Bayesian model analysis, a combination of the spatial feature extraction and the support vector machine, or the like.

A classification accuracy refers to a metric used to evaluate a model and/or an algorithm. In some embodiments, the classification accuracy may represent a percentage of correctly predicted results by the model and/or algorithm. Merely by way of example, for the binary classification problem, the classification accuracy may be determined as: Accuracy=(TP+TN)/(TP+TN+FP+FN). Wherein, TP (True Positive) denotes a count of samples that are actually positive and correctly predicted as positive; TN (True Negative) denotes a count of samples that are actually negative and correctly predicted as negative; FP (False Positive) denotes a count of samples that are actually negative but incorrectly predicted as positive; and FN (False Negative) denotes a count of samples that are actually positive but incorrectly predicted as negative.

In some embodiments, the classification accuracies of the plurality of dimensions may represent a plurality of combinations of feature extraction types and pattern recognition algorithms, where each of the plurality of combinations indicates a proportion of correctly predicted results.

In some embodiments, the control module may obtain the classification accuracies of the plurality of dimensions obtained in the process of verifying the separability of the features in the following manner. The following description uses obtaining the classification accuracy of Dimension A (corresponding to the combination of the frequency domain feature extraction and support vector machine) as an example.

S1: the frequency domain feature extraction may be performed on the EEG data collected by the signal acquisition component, and the EEG data with a specific frequency band may be obtained after feature extraction;

S2: a support vector machine may be trained based on the feature-extracted EEG data with the specific frequency band, where the support vector machine may be a machine learning model;

In some embodiments, an input of the support vector machine may include the feature-extracted EEG data of the specific frequency band, and an output of the support vector machine may include a feature category corresponding to the feature-extracted EEG data of the specific frequency band.

In some embodiments, the support vector machine may be obtained based on a large number of samples trained with labels. The samples may include the EEG data with the specific frequency band after sample features have been extracted, and the labels may include actual feature categories corresponding to the samples.

In some embodiments, the samples may be determined based on historical data, and the labels may be constructed based on the actual feature categories corresponding to the samples.

In some embodiments, the control module may input the samples into an initial support vector machine, update parameters of the initial support vector machine through iterations of training until the trained model satisfies a preset training condition, and obtain the trained support vector machine. The preset training condition may include a loss function being less than a threshold or converging, a training cycle reaching a threshold, or the like. In some embodiments, a technique for iteratively updating the parameters of the model may include a conventional model training technique such as stochastic gradient descent.

S3: a proportion of correctly predicted results by the support vector machine, i.e., the classification accuracy of Dimension A may be determined.

The correctly predicted results by the support vector machine refer to prediction results where feature categories outputted by the support vector machine align with actual feature categories. The proportion of correctly predicted results by the support vector machine refers to a ratio of a count of results predicted correctly by the support vector machine to a total count of predicted results.

In some embodiments, the control module may obtain the classification accuracy of Dimension A by comparing the count of feature categories output by the support vector machine that align with the actual feature categories (i.e., the count of results correctly predicted by the support vector machine) and the total count of results predicted by the support vector machine during a preset time period, and then determine the proportion of correctly predicted results by the support vector machine by a quotient, thereby obtaining the classification accuracy of Dimension A.

Understandably, by determining the classification accuracy for each of the plurality of dimensions in the manner described above, the classification accuracies for the plurality of dimensions may be obtained.

The average accuracy refers to an average of the classification accuracies of the plurality of dimensions. In some embodiments, the control module may determine the average accuracy based on the classification accuracies of the plurality of dimensions. The amplification rate adjustment instruction refers to an instruction for adjusting a signal amplification rate of the EEG amplifier to a target amplification rate. The signal amplification rate refers to the signal amplification rate of the EEG amplifier. In some embodiments, the signal amplification rate may be set manually in advance. The target amplification rate refers to the signal amplification rate of the EEG amplifier that satisfies a first control relationship. In some embodiments, the first control relationship may be determined based on a historical signal amplification rate of the EEG amplifier and a historical average accuracy.

The sampling rate adjustment instruction refers to an instruction for adjusting a sample rate of the signal acquisition component to a target sample rate. The sampling rate refers to the frequency at which the signal acquisition component collects data (e.g., EEG data during speech imagery). In some embodiments, the sampling rate may be manually set in advance. The target sampling rate refers to the sampling rate of the EEG amplifier that satisfies a second control relationship. In some embodiments, the second control relationship may be determined based on a historical sampling rate of the signal acquisition component and a historical average accuracy.

In some embodiments, the control module may generate the amplification rate adjustment instruction and/or the sampling rate adjustment instruction via a preset table in response to determining that the average accuracy is below a first threshold. For example, the control module may, in response to determining that the average accuracy is below the first threshold, generate the amplification rate adjustment instruction or the sampling rate adjustment instruction via the preset table. As another example, the control module may, in response to determining that the average accuracy is below the first threshold, generate the amplification rate adjustment instruction and the sampling rate adjustment instruction via the preset table.

The preset table represents a correspondence between average accuracies and amplification rate adjustment instructions and/or sampling rate adjustment instructions, where each accuracy average corresponds to an amplification rate adjustment instruction and/or a sampling rate adjustment instruction. In some embodiments, the preset table may be constructed based on a historical signal amplification rate of the EEG amplifier and/or a historical sampling rate of the signal acquisition component and a historical average accuracy.

In some embodiments, the first threshold may be set manually in advance based on historical experience, etc.

In some embodiments, the control module may automatically send the amplification rate adjustment instruction and/or the sampling rate adjustment instruction to the EEG amplifier and/or the signal acquisition component, respectively, and control the EEG amplifier and/or the signal acquisition component to execute the corresponding instruction.

As described above, the classification accuracy represents a percentage of correctly predicted results by a model and/or an algorithm. Therefore, the classification accuracy may also be used to assess the separability of samples. For example, if a model (e.g., a support vector machine) trained by a processor using a batch of samples (e.g., the EEG data with the specific frequency band after feature extraction) has a low classification accuracy, the separability of the batch of samples is low or even non-existent. Reasons for the low separability of the samples may include excessive noise (e.g., external interference during data acquisition) in original data (e.g., the EEG data during speech imagery), a large amount of repetitive data in the original data (e.g., insufficient amplification of signals in the EEG amplifier), and an insufficient amount of data in the original data (e.g., insufficient sampling rate of the signal acquisition component).

Therefore, the processor may utilize different dimensions (i.e., different combinations of feature extraction types and pattern recognition algorithms) to verify the separability of the EEG data obtained after feature extraction, and if the average accuracy of classification accuracies obtained from a plurality of verifications is low, it may indicate that the problem lies not with the selection of pattern recognition algorithms but rather with issues in the original data. Accordingly, the processor may obtain classification accuracies of a plurality of dimensions during the process of verifying the separability of the features and determine an average accuracy. If the average accuracy is lower than the first threshold, the processor may generate an amplification rate adjustment instruction and/or a sampling rate adjustment instruction to adjust a corresponding parameter of the EEG amplifier and/or the signal acquisition component, thereby avoiding defects in the original data to a certain extent.

In some embodiments, the control module may further generate the amplification rate adjustment instruction and/or the sampling rate adjustment instruction in response to the accuracy rate average falling below the first threshold. For example, the control module may randomly generate a plurality of candidate value sets in response to the average accuracy falling below the first threshold, where each candidate value set includes a candidate amplification rate and a candidate sampling rate. For each of the plurality of candidate value sets, the control module may predict a first accuracy corresponding to the candidate value set using a prediction model. Then the control module may determine a target value set based on first accuracies corresponding to the plurality of candidate value sets, and generate the amplification rate adjustment instruction and/or the sampling rate adjustment instruction based on the target value set.

A candidate value set is a combination of a candidate amplification rate and a candidate sampling rate. In some embodiments, each of the plurality of candidate value sets includes a candidate amplification rate and a candidate sampling rate. In some embodiments, the control module may randomly generate a plurality of candidate value sets. In some embodiments, the plurality of candidate value sets may be manually set in advance based on historical experience.

The first accuracy corresponding to a candidate value set refers to an estimated value of the average accuracy of classification accuracies of a plurality of dimensions during the process of verifying the separability of features, when the EEG data collected by the EEG amplifier and the signal acquisition component are operated with the candidate value set. In some embodiments, for each candidate value set, the control module may predict the first accuracy corresponding to the candidate value set using a prediction model.

The prediction model refers to a model used to determine the first accuracy of the plurality of candidate value sets. In some embodiments, the prediction model may be a machine learning model. For example, the prediction model may include one or more of a Deep Neural Network (DNN) model, a Convolutional Neural Networks (CNN) model, a customized model, or any combination thereof.

In some embodiments, an input of the prediction model may include a plurality of candidate value sets, and an output of the prediction model may include the first accuracy of each of the plurality of candidate value sets.

In some embodiments, the input of the prediction model may further include an environmental noise characteristic and a subject hair characteristic.

The environmental noise characteristic refers to a characteristic related to the interference of EEG data acquisition. Factors that cause interference with EEG data acquisition may include environmental sound, temperature, lighting, or the like. In some embodiments, the environmental noise characteristics may include a sequence of voltage data, with a voltage value at each moment reflecting an intensity of environmental noise at the moment.

In some embodiments, the environmental noise characteristic may be obtained by data acquisition of a control group by the signal acquisition component. The control group may be a test environment with no subject participation. For example, the signal acquisition component may be worn on the head of a dummy model, and the sequence of voltage data acquired by the signal acquisition component during a preset time period may be designated as the environmental noise characteristic.

Due to the interference of environmental noise (e.g., the environmental sound, temperature, lighting, etc., mentioned before), weak voltages may be spontaneously generated near electrodes of the signal acquisition component, and the weak voltages may be recorded when the signal acquisition component collects the EEG data (i.e., the weak voltages are included in the EEG data). Therefore, by separately collecting the weak voltages through the signal acquisition component, the environmental noise characteristic may be obtained.

The subject hair characteristic refers to a characteristic that reflects density of the subject's hair. In some embodiments, the subject hair characteristic may be obtained by manual input, image recognition, or the like.

In some embodiments of the present disclosure, incorporating the environmental noise characteristic and the subject hair characteristic as inputs of the prediction model can improve prediction accuracy of the prediction model.

In some embodiments, the prediction model may be obtained by training based on a large number of training samples with labels. The training samples may be signal amplification rates of the EEG amplifier and sampling rates of the signal acquisition component during historical experiments. The label of a sample may be an average accuracy of N×M classification accuracies obtained from N independent EEG data collections in a historical scenario corresponding to the training sample, with M separability verifications for each EEG data collection.

In some embodiments, when the input of the prediction model includes environmental noise characteristic and the subject hair characteristic, the training samples may further include environmental noise characteristics and subject hair characteristics during the historical experiment.

In some embodiments, the label corresponding to each training sample may be determined based on N×M classification accuracies obtained from N independent EEG data collections in a historical scenario corresponding to the training sample, with M separability verifications for each EEG data collection. The training samples may have the same or different N and M values, with the N value of each training sample being related to a dispersion degree of sample environmental noise characteristics in the training sample.

Taking training a sample A as an example, in a historical scenario corresponding to training the sample A, suppose that five EEG data collections is performed and six separability verifications may be performed for each of the five EEG data collections. That is to say, a total of [5×6]=30 classification accuracies may be obtained, and the average accuracy of the 30 classification accuracies may be determined as a label for training the sample A.

The dispersion degree of the sample environmental noise characteristics refers to a degree to which the sample environmental noise characteristics are dispersed. In some embodiments, the dispersion degree of the sample environmental noise characteristics may be represented by a variance or a standard deviation. In some embodiments, the control module may obtain the dispersion degree of the sample environmental noise characteristics by determining the variance or the standard deviation of the sample environmental noise characteristics (e.g., the sequence of voltage data).

In some embodiments, the N value for each training sample may be positively correlated with the dispersion degree of the sample environmental noise characteristics in the training sample. The greater the dispersion degree of the sample environmental noise characteristics, the greater the N value of the training sample. In other words, due to significant instability of environmental noise, it is necessary to increase the N value of the training sample so that the situation reflected in the training sample is more average and realistic, which is conducive to improving the prediction accuracy of the prediction model.

In some embodiments, a training process of the prediction model may include:

In 1: a training dataset may be obtained. The training dataset may include a plurality of training samples and the label corresponding to each of the plurality of training samples.

In 2: multiple rounds of iterations may be performed, where at least one round of iterations may include:

(1) selecting at least one training sample from the training dataset and inputting into an initial prediction model, and obtaining a model prediction output corresponding to the at least one training sample.

(2) substituting the model prediction output corresponding to the at least one training sample and the label corresponding to the at least one training sample into a loss function calculation formula to obtain a value of the loss function.

(3) based on the value of the loss function, updating a parameter of the initial prediction model in reverse. A technique for iteratively updating the model parameter may include a conventional model training technique such as stochastic gradient descent.

In 3: When an iteration end condition is satisfied, stopping the iteration and obtaining a trained prediction model. The iteration end condition may include the loss function being less than a threshold or converging, a training cycle reaching a threshold, or the like.

In some embodiments of the present disclosure, the trained prediction model can quickly and accurately predict the first accuracy for each candidate value set, thereby laying the foundation for the final determination of the target value set.

The target value set is a combination of a target amplification rate and a target sampling rate. In some embodiments, each target value set may include a target amplification rate and a target sampling rate. More descriptions of the target amplification rate and the target sampling rate may be found in the related descriptions above.

In some embodiments, the control module may determine, based on first accuracies corresponding to a plurality of candidate value sets, a candidate value set with a highest first accuracy as the target value set.

In some embodiments, the control module may determine, based on the first accuracies corresponding to the plurality of candidate value sets, a candidate value set with a first accuracy greater than a preset threshold value and having a smallest candidate sampling rate as the target value set. By adopting this approach, it is possible to ensure the first accuracy to a certain extent while reducing the amount of data, thereby optimizing the use of computational resources for subsequent analysis.

In some embodiments, the control module may automatically generate the amplification rate adjustment instruction and/or the sampling rate adjustment instruction based on the target value set through code.

In some embodiments of the present disclosure, by predicting first accuracies corresponding to a plurality of candidate value sets through the prediction model, and then determining the target value set based on the first accuracies, the amplification rate adjustment instruction and/or the sampling rate adjustment instruction may be generated quickly, thereby ensuring adjustment accuracy while improving an adjustment speed of the EEG amplifier and the signal acquisition component.

Figure 8:
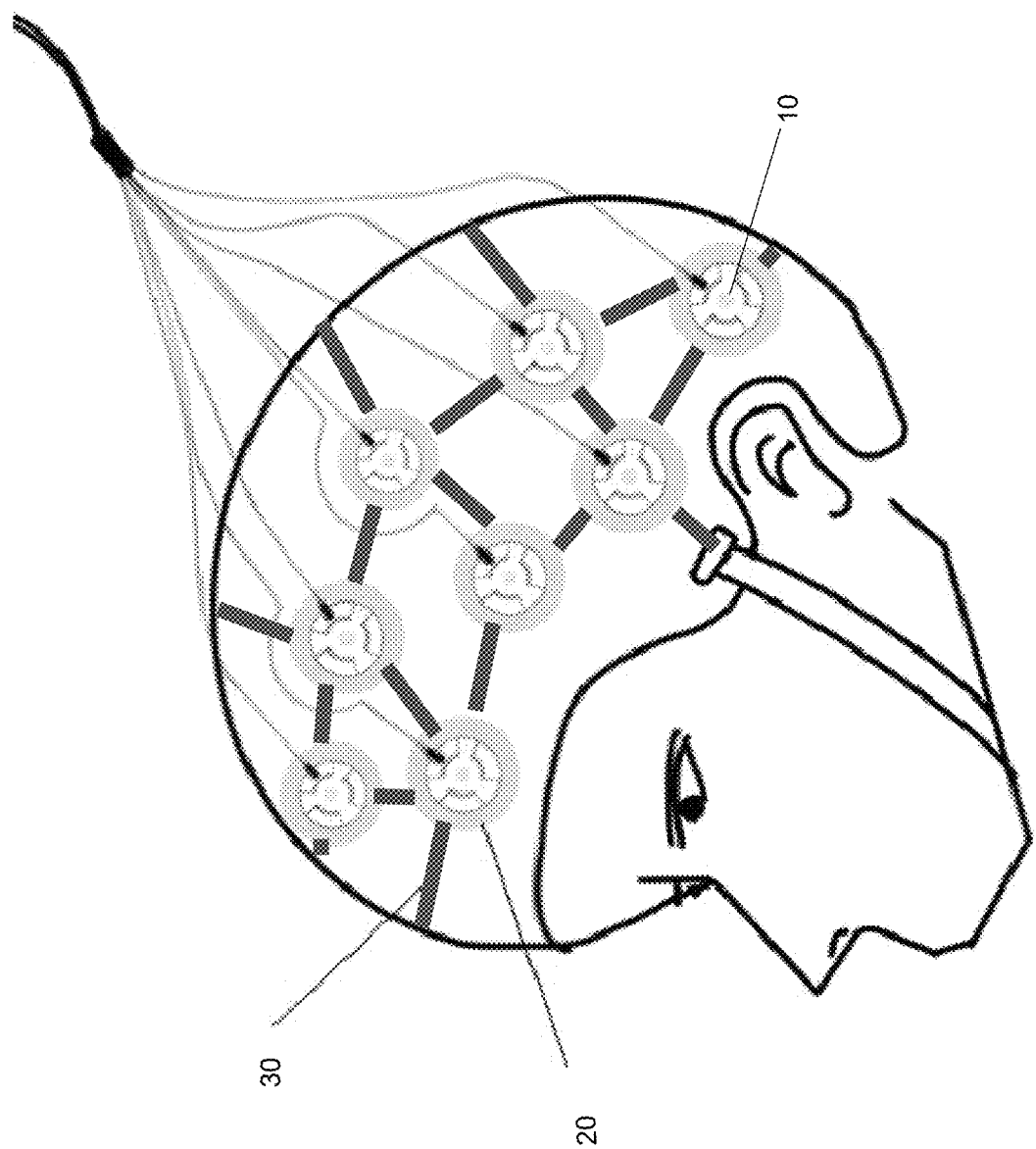
FIG. 8 is a schematic diagram of a structure of a signal acquisition component according to some embodiments of the present disclosure.

FIG. 8 is a schematic diagram of a structure of a signal acquisition component according to some embodiments of the present disclosure.

In some embodiments, as shown in FIG. 8, the signal acquisition component includes a plurality of disk electrodes 10, a plurality of disk electrode slots 20 securing the plurality of disk electrodes 10, and a plurality of telescopic elastic connection strips 30 connecting the plurality of disk electrode slots 20. The plurality of telescopic elastic connection strips 30 may be communicatively connected to the control module.

The disc electrode 10 refers to a signal input point of the signal acquisition unit, which is used to receive electrical signals of brain neurons during speech imagery, i.e., EEG data during speech imagery. In some embodiments, each disc electrode 10 of the plurality of disc electrodes 10 may be coupled to one of a plurality of interfaces of an EEG amplifier for transmitting the collected EEG data to the EEG amplifier, and the EEG amplifier may amplify the collected EEG data to enhance detection sensitivity and accuracy of the signal.

The disc electrode slot 20 refers to a slot structure for securing the disc electrode 10. More descriptions of the disc electrode slot may be found in the subsequent related descriptions.

The telescopic elastic connection strip 30 refers to a connection structure for connecting the disc electrode slots 20. In some embodiments, a disc electrode slot 20 may be connected to at least one telescopic elastic connection strip 30.

In some embodiments, the control module may be further configured to: determine a target disc electrode based on an analysis result of preprocessing of the EEG data, generate a contraction adjustment instruction, and send the contraction adjustment instruction to the disc electrode slot connected to at least one telescopic elastic connecting strip connected to the disc electrode slot where the target disc electrode is located.

The analysis result of the preprocessing of the EEG data refers to processed data obtained after the significance feature screening and verification module preprocesses the EEG data. In some embodiments, the control module may obtain the analysis result of the preprocessing of the EEG data from the significance feature screening and verification module. More descriptions of the preprocessing process may be found in FIG. 1 and the related descriptions thereof.

The target disk electrode refers to a disk electrode with an abnormal condition. For example, the abnormal condition may include, but is not limited to, poor contact or the like.

In some embodiments, the control module may determine, based on the analysis result of the preprocessing of the EEG data, a disk electrode corresponding to data that satisfies a preset condition in the analysis result as the target disk electrode. The preset conditions may include missing of data in the analysis result or data (e.g., amplitude) exceeding an abnormal threshold. In some embodiments, the abnormal threshold may be manually set in advance based on historical experience.

The contraction adjustment instruction refers to an instruction related to adjusting at least one telescopic elastic connection strip connected to the disc electrode slot where the target disc electrode is located. In some embodiments, the contraction adjustment instruction may be used to make the at least one telescopic elastic connection strip to tighten with a preset tightening amplitude.

In some embodiments, in response to determining that the target disc electrode exists, the control module may automatically generate and send the contraction adjustment instruction to the at least one telescopic elastic connection strip connected to the disc electrode slot where the target disc electrode is located, thereby making the at least one telescopic elastic connection strip to tighten with the preset tightening amplitude.

In some embodiments, the preset tightening amplitude may be set manually in advance based on historical experience. In some embodiments, the preset tightening amplitude may be determined based on a size of an outer contour of the head of the subject. For example, the larger the outer contour of the head of the subject is, the larger the preset tightening amplitude may be. In some embodiments, the size of the outer contour of the head of the subject may be determined through image recognition, or the like.

It may be understood that if a poorly contacting disc electrode (i.e., the target disc electrode) exists, it may be that the location or area where the electrode is located is not worn tightly enough, and the contact pressure with the subject is not sufficient. Therefore, by tightening at least one telescopic elastic connection strip to a preset tightening amplitude, the poorly contacting disc electrode may be tightened to increase the contact between the disc electrode and the subject's head (e.g., the scalp), thus avoiding poorly contacting disc electrodes that affect EEG data collection.

In some embodiments, a vibration component may be provided in each pf the plurality of disk electrode slots 20, and the control module may be communicatively connected to the vibration component.

The vibration component refers to a component for generating vibrations. Exemplary vibration components may include shakers, vibrators, or the like. In some embodiments, the vibration component may be disposed at any feasible location within the disk electrode slot.

In some embodiments, the control module may be further configured to: determine a target disc electrode based on an analysis result of the preprocessing of the EEG data, generate a vibration instruction, and send the vibration instruction to a vibration component in a disc electrode slot where the target disc electrode is located. More descriptions of determining the target disk electrode may be found in the preceding related descriptions.

The vibration instruction refers to an instruction related to controlling the vibration of a vibrating component associated with a disk electrode slot in which the target disk electrode is located. In some embodiments, the vibration instruction may be used to make the vibration component to vibrate at a preset amplitude for a preset time.

In some embodiments, the control module may, in response to determining that the target disk electrode exists, automatically generate the vibration instruction and send the vibration instruction to the vibration component in the disk electrode slot in which the target disk electrode is located to make the vibration component to vibrate at the preset amplitude for the preset time. In some embodiments, the preset amplitude and the preset time may be set manually in advance based on historical experience.

In some embodiments, when the signal acquisition component is worn on the head of the subject, it is often necessary to apply a conductive paste to the disk electrodes of the signal acquisition component to ensure better signal transmission from the head (e.g., the scalp) of the subject to the disk electrodes. Therefore, poor contact of the disk electrodes may also be caused by uneven application of the conductive paste, resulting in inadequate conduction pathways between the disc electrodes and the scalp. In such cases, controlling the vibration components inside the disc electrode slots to vibrate can help redistribute the conductive paste evenly, thereby further improving poor contact of the disc electrodes and enhancing the integrity and efficiency of data collection.

Some embodiments of the present disclosure further provide a method for controlling a speech brain-computer interface neural decoding system based on Chinese language, including:

In 1: collecting EEG data during speech imagery from a specific population. The specific population refers to patients with speech disorders and other groups of people who cannot vocalize normally.

In 2: performing feature extraction on features from the EEG data, and screening the features to obtain EEG data with a specific frequency band or EEG data within a brain region.

In 3: obtaining speech spectrum information by inputting the EEG data with the specific frequency band or the EEG data within the brain region into a speech imagery semantic decoder for decoding and reconstructing.

In 4: synthesizing the speech spectrum information into real speech using a speech synthesis technology, and completing an end-to-end output of the EEG data to the real speech. Exemplary speech synthesis technologies may include a WaveNet vocoder, a WaveRnn vocoders, or the like.

Some embodiments of the present disclosure further provide a method for implementing a speech brain-computer interface neural decoding system based on Chinese language, including:

In 1: Constructing a Speech Imagery EEG Database

According to an experimental paradigm design, EEG data of a subject during speech imagery and normal vocalization and speech data of the subject during normal vocalization may be collected to construct the speech imagery EEG database.

In 2: Extracting Brain Regions and Rhythmic Features Closely Related to Speech Imagery Activities Frequency domain feature extraction and spatial feature extraction may be performed on the EEG data in the speech imagery EEG database. Then, a pattern recognition algorithm may be used to verify the separability of obtained EEG features and to screen the features to obtain EEG data with a specific frequency band or EEG data within a brain region. At the same time, a long and short-term memory (LSTM) network may be used to extract an acoustic feature of speech data corresponding to the EEG data with the specific frequency band or the EEG data within the brain region.

During a training process of a speech imagery semantic decoder, due to the relatively low quality of the EEG signals and their susceptibility to artifacts such as EMG signals, and the limitation in decoding accuracy caused by single-dimensional information, a separate long and short-term memory (LSTM) network may be introduced in the speech imagery EEG data decoding module. A statistical technique may be used to estimate vocal tract movement trajectories (e.g., lip, tongue, and jaw movements) and other physiological features (e.g., pronunciation style) in audio recordings. The LSTM network may be used to extract the acoustic feature (e.g., pitch (F0), low-frequency cepstrum coefficients (MFCCs), or the like) from the audio recordings.

In 3: Constructing the Speech Imagery Semantic Decoder

By designing a single end-to-end architecture using a deep learning algorithm and determining a generic task of neural decoding, the speech imagery semantic decoder may be initially constructed.

In 4: Training and Transferring the Speech Imagery Semantic Decoder

The training process of the speech imagery semantic decoder is shown in FIG. 2. Firstly, the EEG data with the specific frequency band or the EEG data within the brain region obtained in the operation 2 may be calibrated and aligned with the acoustic feature obtained from the corresponding speech data extracted through the LSTM network to establish a mapping relationship. Then, the aligned data may be divided into a training set, a validation set, and a test set. Data in the training set may be input into the constructed speech imagery semantic decoder to reconstruct and obtain speech spectrum information corresponding to the EEG data with the specific frequency band or the EEG data within the brain region, and comparative learning training may be performed on the speech imagery semantic decoder. Finally, validation and testing may be performed using the validation set and the test set.

Due to the individual differences in the brains of different subjects, differences in sensor placement, and variations in acoustic features, the parameter of the decoder trained on different subjects' EEG data may be different. By sharing the acoustic features among subjects, a parameter corresponding to an optimal decoding performance may be used as initialization. Then, fine-tuning may be performed when training EEG data of other subjects, and transfer learning may be used to accelerate model convergence and improve a generalization ability of the speech imagery semantic decoder.

In 5: Integrating the Speech Brain-Computer Interface Neural Decoding System

The EEG data acquisition, EEG feature extraction, EEG feature screening, and the constructed speech imagery semantic decoder in the steps described above may be integrated to obtain a communication-assistive speech brain-computer interface neural decoding system that conforms to a natural vocalization mode and has a high communication rate.

Specifically, in the operation 2, the EEG data is typically divided into five frequency bands, i.e., Delta (0.5-4 Hz), Theta (4-8 Hz), Alpha (8-12 Hz), Beta (12-30 Hz), and Gamma (>30 Hz). In some embodiments, an autoregressive (AR) model may be used to perform power spectral analysis on the EEG data for frequency domain feature extraction: first, a specific parametric model is first used to describe the data, then a model parameter may be estimated from the EEG data, and finally, the estimated model parameter may be used to compute the signal spectrum in the specific frequency band.

In some embodiments, a commonly used order P AR model may be represented as AR(P), where x(n) denotes a random signal, $b_p$ denotes a coefficient of the AR model (p=1, 2, . . . , P), and x(n) consists of a linear combination of random noise p(n) and a plurality of pieces of observed signal data x(n-p) before the random noise p(n), as shown in Equation 1:

$$x(n) = p(n) + \Sigma_{p=1}^{P} b_p x(n-p) \quad (1)$$

The AR coefficient $b_p$ may be solved by the Yule-Walker technique, Levinson-Durbin technique, Burg technique, covariance technique, and modified covariance technique. In this embodiment, the AR coefficient is estimated using the Yule-Walker technique, and under the premise that the AR coefficient has already been estimated, the spectrum of the random signal x(n) may be computed from the AR coefficient using Equation 2:

$$p(f) = \sigma_p^2 \left| \frac{1}{1 + \sum_{p=1}^{p} \frac{b_p e^{-j2\pi f p}}{Fs}} \right|^2 \quad (2)$$

wherein $\sigma_p^2$ denotes the variance of the random noise p(n), f denotes a signal frequency, p denotes a power value, Fs denotes a signal sampling rate, and j denotes a time series. Different model orders P may greatly affect the result of AR spectrum estimation. The higher the model order is, the smaller the residual unexplained variance of the signal and the more accurate the model is. However, an excessively high model order may increase estimation variance of the model. In this embodiment, a plurality of model orders are attempted to determine the optimal model order for the AR model. Based on the above principle, power spectra of different frequency bands of EEG signals may be computed, and differences in brain region activation for different frequency bands may be visualized.

In addition, in the operation 2, Granger causality-based indexes may be selected to measure a causal relationship and an information flow direction between different neural oscillatory activities to identify a connectivity index that is closely related to speech imagery. Granger defines the causal relationship in a time series based on the following assumptions: (1) A cause necessarily precedes its effect or result; (2) In predicting the effect, the cause can improve a prediction accuracy of the effect by providing information not available from the past of the effect.

Preliminary frequency domain features and connectivity indexes closely related to speech imagery EEG data may be obtained. Feasibility of the screened features was verified using a pattern recognition algorithm. By designating the extracted features as class labels for speech imagery EEG signals and training the filtered EEG data using a classifier to obtain a weight for each feature, a mapping relationship between the features and class labels may be established. A cross-validation technique may be used to train and test with all the data, thoroughly considering the classifier's ability to correctly identify training data categories and generalization effect, thus avoiding overfitting. To verify the separability of the screened features, a relatively simple support vector machine may be used for multi-class classification, and a Receiver Operating Characteristic (ROC) curve may be used to evaluate a classification result, determining an importance level and significance of the features for classification. This approach aims to identify the brain regions and frequency bands associated with speech imagery while reducing data dimensionality and significantly decreasing the computational load for subsequent decoding tasks.

In some embodiments, a construction process of the speech imagery EEG database is described below.

Based on the practicality of assistive communication, a corpus of Chinese language speech imagery may be established. High-frequency characters, words, and short phrases suitable for the target population of the corpus may be selected, considering the tonal language nature of Chinese. The basic guidelines for corpus selection were proposed as shown in Table 1:

TABLE 1

Basic Guidelines for Corpus Selection

| Number | Basic Guideline |
| --- | --- |
| 1 | Structurality: selection according to characters, words, and short phrases structures, respectively |
| 2 | Metadata: considering factors such as time, geography, etc. |
| 3 | Scale: corpus size determined by practical considerations |
| 4 | Representativeness: selection of high-frequency corpus |
| 5 | Practicality for assistive communication: avoid written language and dialects |
| 6 | Specificity: avoid difficult-to-distinguish retroflex and nasal sounds |

The selection of a corpus generally requires completeness and exhaustiveness, aiming to study both the overall patterns of a language and its diversity. However, some embodiments of the present disclosure aim to study the patterns of speech imagery in specific populations, and thus propose the above basic guidelines for selecting the corpus.

An inclusion criterion for the subject is an absence of any history of hearing or visual impairment, neurological disorders, or other speech disorders.

Chinese materials may be selected according to the structure of single characters, words, and short phrases. Specific prompt materials may be selected based on the established corpus screening criterion, choosing simple single Chinese characters such as "上 (up)," "下 (down)," "左 (left)," and "右 (right)"; high-frequency words used in daily life such as "你好 (hello)," "学校 (school)," "医院 (hospital)," "电视 (television)," and "闹钟 (alarm clock)"; and words from different categories or parts of speech, such as animals and plants, nouns and verbs, respectively, as experimental materials. Taking the selection of words as an example, a 2-second auditory cueing vocalization material and a corresponding visual cueing material may be selected to prompt a subject to speak. Through a preliminary experiment and feedback from the subject and EEG responses, the experimental paradigm may be refined to eliminate irrelevant factors as much as possible, ultimately determining more than 10 instructions that reflect different levels of difficulty.

EEG responses during actual speech are valuable for understanding speech imagery. Therefore, while conducting speech imagery experiments, a normal vocalization group may be set up. The aim is to identify leads involved in speech production and recognition and to find a correlation between EEG data of normal vocalization and EEG data of speech imagery, which facilitates the establishment of a more robust EEG classification and decoding model for speech imagery. Specifically, an experimental paradigm design of this study includes the following two modes: (1) Normal vocalization, where subjects receive auditory and visual prompts and repeat the heard content (requiring vocalization); (2) Speech imagery, where subjects receive auditory and visual prompts and imagine the speech without actual vocalization, silently reading the prompted material in their mind without making any sound, and keeping the speech organs and facial muscles still. The subjects are informed that they only need to perform the normal (imagined) speech once before the experiment. Based on the above experimental paradigm design, the corresponding speech imagery EEG database may be constructed.

The experimental process is as follows: Before the experiment begins, the subjects are required to remain at rest and prepare to perceive a target speech. Auditory cueing vocalization materials are then played randomly without repetition, and the subjects are instructed on the speech rate and manner of articulation for both normal vocalization and speech imagery, all to be completed within 2 seconds. After the playing of the auditory cueing vocalization materials ends, standardized visual cueing materials are also presented randomly without repetition. The subjects perform both normal vocalization and speech imagery tasks. The visual cueing material disappears 1 second after appearing, giving the subjects 2 seconds to complete the normal vocalization or speech imagery task. EEG data is recorded throughout the experiment using a 64-channel Neuroscan EEG acquisition device (with a sampling rate of 1 kHz and electrodes covering the entire head). A microphone is used to verify that no audible sound is made during speech imagery and to monitor behaviors (e.g., onset time of vocalization and word length) of the subjects during normal vocalization.

During the experiment, both the tasks and EEG acquisition device are designed to account for the subjects' cognitive load. After completing each set of experiments, the subjects may choose to take a break, thereby reducing an impact of EEG time-related variability on the experiment.

In the aforementioned experiment, the auditory cueing vocalization materials and visual cueing materials are selected according to the corpus screening guidelines.

The beneficial effects of the speech brain-computer interface neural decoding system based on Chinese language and its control and implementation methods provided in the present disclosure may include but are not limited to: (1) The speech brain-computer interface neural decoding system based on Chinese language provided in some embodiments of the present disclosure provide a natural and intuitive auxiliary communication tool for patients with speech disorders. Its control method is more intuitive, requiring no training for the subjects and not relying on a specific measurement environment. The speech brain-computer interface neural decoding system is more natural and intuitive, with a high communication speed and a high degree of freedom, and can be widely applied. (2) The speech brain-computer interface neural decoding system based on Chinese language provided in some embodiments of the present disclosure integrates the EEG data acquisition, EEG feature extraction, EEG signal decoding for reconstructing the speech spectrum information, and understandable speech synthesis. After obtaining the reconstructed spectrogram features, Pearson correlation analysis is performed with the original spectrogram features, with a correlation typically ≥80%. The decoding performance of the speech brain-computer interface neural decoding system (e.g. the speech imagery semantic decoder) has been verified to be better than the performance of traditional decoding models, enabling the speech brain-computer interface neural decoding system to effectively improve the communication capability of speech-impaired patients with the outside world.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this disclosure are not necessarily all referring to the same embodiment. Furthermore, the particular features, structures, or characteristics may be combined as suitable in one or more embodiments of the present disclosure.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

As another example, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This way of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the present disclosure are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameter set forth in the written description and attached claims are approximations that may vary depending upon the desired properties sought to be obtained by a particular embodiment. In some embodiments, the numerical parameter should be construed in light of the number of reported significant digits and by applying ordinary rounding techniques. Notwithstanding that the numerical ranges and parameter setting forth the broad scope of some embodiments of the present disclosure are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the present disclosure disclosed herein are illustrating of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A brain-computer interface (BCI) control system, comprising:
    an electroencephalography (EEG) data acquisition module configured to collect EEG data during speech imagery;
    a significance feature screening and verification module configured to perform feature extraction on features from the EEG data, verify separability of the features, and screen the features to obtain EEG data with a specific frequency band or EEG data within a brain region;
    a speech imagery EEG data decoding module configured to obtain, by inputting the EEG data with the specific frequency band or EEG data within the brain region into a speech imagery semantic decoder for decoding and reconstructing, speech spectrum information, wherein the speech imagery semantic decoder includes a spatial attention layer, a convolutional layer, a subject layer, a convolutional block, a BatchNorm layer, a GELU activation layer, and two 1×1 convolutional layers; and
    an understandable speech synthesis module configured to synthesize the speech spectrum information into real speech using a speech synthesis technology;
    wherein a decoding process of the speech imagery semantic decoder includes:
        remapping the EEG data with the specific frequency band or the EEG data within the brain region onto the spatial attention layer;
        outputting the EEG data with the specific frequency band or the EEG data within the brain region to the convolutional layer for convolution via Fourier spatial parameterization of each output channel of the spatial attention layer, respectively, and reducing dimensionality of the EEG data at the same time;
        aligning EEG signals in a common space by training using the subject layer;
        performing convolution by using the convolutional block;
        halving a count of channels using the BatchNorm layer and the GELU activation layer; and
        utilizing an inter-object variability by applying the two 1×1 convolutional layers, outputting a matching speech representation, and utilizing a wav2vec 2.0 speech algorithm for automatic learning to obtain the speech spectrum information.

2. The brain-computer interface (BCI) control system of claim 1,
wherein the feature extraction includes frequency domain feature extraction and spatial feature extraction;
the frequency domain feature extraction is performed to obtain a signal spectrum with the specific frequency band by performing power spectrum analysis on the EEG data using an autoregressive model; and
the spatial feature extraction is performed to identify a connectivity index closely related to the speech imagery by adopting brain network connectivity analysis and selecting a Granger causality-based index to measure a causal relationship or an information flow direction between different neural oscillatory activities.

3. The brain-computer interface (BCI) control system of claim 1, wherein a count of channels of the spatial attention layer is the same as a count of sensor channels for original collection of the EEG data; and the convolutional block includes three convolutional layers.

4. The brain-computer interface (BCI) control system of claim 1, wherein the EEG data acquisition module, the significance feature screening and verification module, the speech imagery EEG data decoding module, and the understandable speech synthesis module are integrated in a visualization program to obtain the brain-computer interface control system.

5. A method for controlling the brain-computer interface (BCI) control system of claim 1, comprising:
collecting EEG data during speech imagery from a specific population;
performing feature extraction on features from the EEG data, and
screening the features to obtain EEG data with a specific frequency band or EEG data within a brain region;
obtaining, by inputting the EEG data with the specific frequency band or the EEG data within the brain region into a speech imagery semantic decoder for decoding and reconstructing, speech spectrum information; and
synthesizing the speech spectrum information into real speech using a speech synthesis technology, and completing an end-to-end output of the EEG data to the real speech.

6. A method for implementing the brain-computer interface (BCI) control system of claim 1, comprising:
according to an experimental paradigm design, collecting EEG data of a subject during speech imagery and normal vocalization and speech data of the subject during normal vocalization, and constructing a speech imagery EEG database;
performing pre-processing and feature extraction on features from the EEG data in the speech imagery EEG database, verifying separability of the features, screening the features to obtain EEG data with a specific frequency band or EEG data within a brain region, and extracting an acoustic feature of speech data corresponding to the EEG data with the specific frequency band or the EEG data within the brain region by using a long and short-term memory (LSTM) network at the same time;
designing a single end-to-end architecture using a deep learning algorithm, determining a generic task of neural decoding, and initially constructing a speech imagery semantic decoder;
training the constructed speech imagery semantic decoder using the EEG data with the specific frequency band or the EEG data within the brain region and the acoustic feature of the speech data corresponding to the EEG data with the specific frequency band or the EEG data within the brain region; and
integrating the EEG data acquisition, the EEG feature extraction, the EEG feature screening, and the speech imagery semantic decoder in the above operations to obtain the brain-computer interface control system.

7. The method of claim 6, wherein, an inclusion criterion for the subject is an absence of any history of hearing or visual impairment, neurological disorders, or other speech disorders; and in the course of an experiment, an auditory cueing vocalization material and a visual cueing material are selected according to corpus screening guidelines.

8. The method of claim 6, wherein, a training process of the speech imagery semantic decoder includes:
calibrating and aligning the EEG data with the specific frequency band or the EEG data within the brain region with the acoustic feature of the speech data corresponding to the EEG data with the specific frequency band or the EEG data within the brain region, and establishing a mapping relationship;
dividing the aligned data into a training set, a validation set, and a test set, inputting data in the training set into the speech imagery semantic decoder, reconstructing and obtaining speech spectrum information corresponding to the EEG data with the specific frequency band or the EEG data within the brain region, and performing comparative learning training on the speech imagery semantic decoder; and
performing validation and testing using the validation set and the test set.

9. The method of claim 8, wherein a model parameter corresponding to an optimal decoding performance is used as initialization during the training process by sharing acoustic features among subjects, then fine-tuning is performed when training EEG data of other subjects, and transfer learning is used to accelerate model convergence and improve a generalization ability of the speech imagery semantic decoder.

* * * * *